(12) United States Patent
Servin de la Mora Godinez et al.

(10) Patent No.: US 10,589,081 B2
(45) Date of Patent: Mar. 17, 2020

(54) PERIPHERAL IV CATHETER WITH BI-VALVE SECURE SYSTEM

(71) Applicants: Pedro Manuel Servin de la Mora Godinez, Jerusalem (IL); Luis Fernando Servin de la Mora Godinez, Jerusalem (IL); Erick Alejandro Servin de la Mora Godinez, Tijuana (MX); Antonio Zavala, Puyallup, WA (US)

(72) Inventors: Pedro Manuel Servin de la Mora Godinez, Jerusalem (IL); Luis Fernando Servin de la Mora Godinez, Jerusalem (IL); Erick Alejandro Servin de la Mora Godinez, Tijuana (MX); Antonio Zavala, Puyallup, WA (US)

( * ) Notice: Subject to any disclaimer, the term of this patent is extended or adjusted under 35 U.S.C. 154(b) by 114 days.

(21) Appl. No.: 14/825,475

(22) Filed: Aug. 13, 2015

(65) Prior Publication Data

US 2016/0106971 A1    Apr. 21, 2016

Related U.S. Application Data

(60) Provisional application No. 62/122,416, filed on Oct. 20, 2014.

(51) Int. Cl.
*A61M 39/26* (2006.01)
*A61M 39/22* (2006.01)

(52) U.S. Cl.
CPC .......... *A61M 39/26* (2013.01); *A61M 39/223* (2013.01); *A61M 2039/229* (2013.01)

(58) Field of Classification Search
CPC ................ A61M 39/26; A61M 39/223; A61M 2039/229
See application file for complete search history.

(56) References Cited

U.S. PATENT DOCUMENTS

| | | | |
|---|---|---|---|
| 4,512,766 A * | 4/1985 | Vailancourt | A61M 39/14 251/149.1 |
| 4,917,671 A * | 4/1990 | Chang | A61M 25/0693 604/168.01 |

(Continued)

*Primary Examiner* — Bradley J Osinski
(74) *Attorney, Agent, or Firm* — The Roy Gross Law Firm, LLC; Roy Gross

(57) ABSTRACT

The Purpose of our devise "Peripheral Intravenous Catheter With an internal Bi-Valvular Secure System" is to Avoid Back-flow spilling of blood or any other biological substance during the insertion of a catheter. Not only the Bi-valvular secure system is adaptable for the use in intravenous or arterial catheters but it can also be adapted to any type of Medical system catheters available in Medical practice due to its unique design, and without the need of changing the complete physical structure of the catheter. The present invention is for Medical field use and it provides a much more sterile and secure approach in reducing the risk of exposure to biological substances while at the same time reducing the risk of contamination to both the patient and the health care provider.
For Purpose of of describing the full operating system of our devise, we have to reiterate that its function is based on the concept of keeping a sterilized access to any Medical System Catheter by avoiding back-flow spilling of any biological substance that could increase the risk of exposure and contamination.

18 Claims, 3 Drawing Sheets

(56) References Cited

U.S. PATENT DOCUMENTS

| | | | | |
|---|---|---|---|---|
| 5,405,323 A * | 4/1995 | Rogers | ............. | A61M 39/0693 |
| | | | | 604/167.04 |
| 9,028,425 B2 * | 5/2015 | Burkholz | ............. | A61B 5/1405 |
| | | | | 600/577 |
| 2002/0128604 A1 * | 9/2002 | Nakajima | ......... | A61M 39/0693 |
| | | | | 604/164.01 |
| 2005/0043684 A1 * | 2/2005 | Basta | .................... | A61M 25/01 |
| | | | | 604/164.13 |
| 2013/0310764 A1 * | 11/2013 | Burkholz | .......... | A61M 25/0045 |
| | | | | 604/246 |

* cited by examiner

PERIPHERAL IV CATHETER WITH BI-VALVE SECURE SYSTEM

DESCRIPTION

The devise is an Adaptable Internal Bi-Valvular Secure System for Medical System Catheters as a hygienic method of containing back-flow secretion and blood spill from a peripheral IV or arterial line while maintaining a sterile peripheral IV or any other medical system catheter in the field and as well as in hospital setting.

FIELD OF INVENTION

The present Invention is for Medical Field use in the trauma or emergency setting, for any hospitalized or ambulatory treatment of any patient. It provides a more sterile and secure approach for peripheral intravenous insertion and any applicable catheter from peripheral and arterial lines, urinary catheters, central lines, ventricular catheters, and biopsy catheters (oncology) by avoiding unnecessary blood spill and the risk of back-flow contamination of biological substances and secretions.

SUMMARY OF THE INVENTION

For purpose of describing the full operating system of our devise, we have to reiterate that its function is based on the concept of keeping a sterilized access to the peripheral vein or arterial line, and to avoid unnecessary stress by the medic or trauma specialist do to constant blood spill once a peripheral or arterial line has been accessed, to keep a sterile access to any other applicable medical systems catheter in use and as well as for the patient, and, to reduce risk of contamination by back-flow spill of any type of biological substance fluid (blood, urine or secretions).

Our devise allows the Medical practitioner to insert any medical systems catheter without any back-flow of biological material and blood exposure that could complicate and compromise securing the catheter, the procedure and the access line.

Our intention is also to reduce the risk of contamination both to the patient and health care provider due to rapid manipulation in order to secure the catheter and/or peripheral line. It avoids putting the physician or paramedic at risk of contamination and reduces the risk of contaminating the patient. In the case where a peripheral line; whether it will be venous or arterial that needs to be accessed, our devise allows the health care provider to insert the peripheral line without any back-flow of blood that could complicate securing the catheter in a trauma like stressful scenario. This Bi-Valvular system will compose the internal structure of a peripheral IV or any other medical system catheter. The structural component of the valve are easy to ensemble at a very low cost due to the fabric of the system that is based on silicon rubber, plastic, and a stainless metal or teflon made spiral. The valvular system is adapted to the peripheral intravenous catheter at the level of the proximal end allowing a connection to the intravenous infusion line below the capping margin, and, allowing a two or three way stopcock to be connected and activating the sliding mechanism of the internalized valvular system. The internal Bi-valve secure system devise can be adapted to any catheter without having to change the structural components and physical shape of any medical systems catheter, only the invented devise will vary in size depending on the type of medical system catheter being displayed in use and allowing a secure connection and a two way flow of the catheter. Using a stopcock or syringe in order to administer or extract biological substance samples, once connected it will push the plastic or silicon sealing adapter located just below the capping margin adapting itself to the proximal portion of the plastic or silicon sealing adapter and sealing the connection (connection between the stopcock or syringe with the plastic or silicon sealing adapter), and at the same time activating the internalized valvular mechanism by pushing distally the plastic or silicon sealing adapter located in the proximal end of the plastic or stainless metal tube container guide and activating the sliding mechanism of the internalized plastic or stainless metal tube container guide. It is precisely from this tube container guide that the needle or guide wire from any medical system catheter is extracted. The role of an internalized plastic tube will as the component responsible to activate the sliding mechanism of the devise which is unique in its function by allowing the opening and closing of the silicon valve. This plastic or stainless metal tube guide will slide supported by the resistant function of the mini spiral band into and through a plastic guide located internally inside the body of the silicon rubber and functioning as the internal skeleton of the silicon valve component. As the plastic or stainless metal tube guide slides distally and in the same automatic fashion when removing the stopcock or any specific connection in between uses causing an automatic proximal retraction, it will open and close a Secure Bi-valve system allowing the access of fluids and medications or, the extraction of blood or any biological samples from any medical system catheter in use. When the stopcock or any other specific connection is removed in between uses, the plastic or silicon seal adapter attached in the proximal end of the tube guide retracts with the resistance support of the Teflon made or stainless metal mini spiral thus retracting the plastic or stainless steal tube guide by sliding proximally in a retroactive fashion through the internal skeleton of the silicon rubber valve and allowing the valve to close and seal automatically the access to the peripheral vein, arterial line or any other medical systems catheter being used for therapeutic reasons. The Teflon made or stainless mini spiral spring band allows the sliding mechanism of the valve to be activated with the appropriate resistance support when medications and/or fluids are administered, and to be deactivated when the IV, arterial line or any other medical system catheter is capped and closed in between uses. The plastic or stainless metal tube guide shelters the needle or guide wire used in any medical systems catheter, and, it is from this same plastic tube container that the needle or guide is retracted from. Unique in its function it allows the retraction and re-insertion of the needle and or guide wire if the need for relocating or re-inserting the catheter is necessary, and this function can be elaborated without damaging the bi-valvular structure and allowing complete manipulation of any type of system catheter. Our devise is activated when an external line is connected via stopcock or any other specific connection to the catheter by sealing to the plastic or silicon sealing adapter and pushing the plastic tube container located just below the capping margin and provoking a sliding mechanism using the teflon made or stainless metal made mini spiral spring band that works as resistance control component.

Through this sliding mechanism, the plastic or stainless metal tube container guide from which the needle or catheter guide wire is retracted from will slide distally through an internalized plastic skeleton centralized internally in the body of the rubber silicon valve and allowing it to push open the silicon valve. Through this same mechanism the plastic tube will be able to slide proximally retracting and closing the bi-valve. This will reduce exposure and risk of contamination in between uses.

BRIEF DESCRIPTION OF THE DRAWINGS

In FIG. 2 the entire Internal Mechanism is reconstructed, The exploded structures of the valve are labeled from (A) to (F) and represents the sliding mechanism of the valve.

Figure 1:
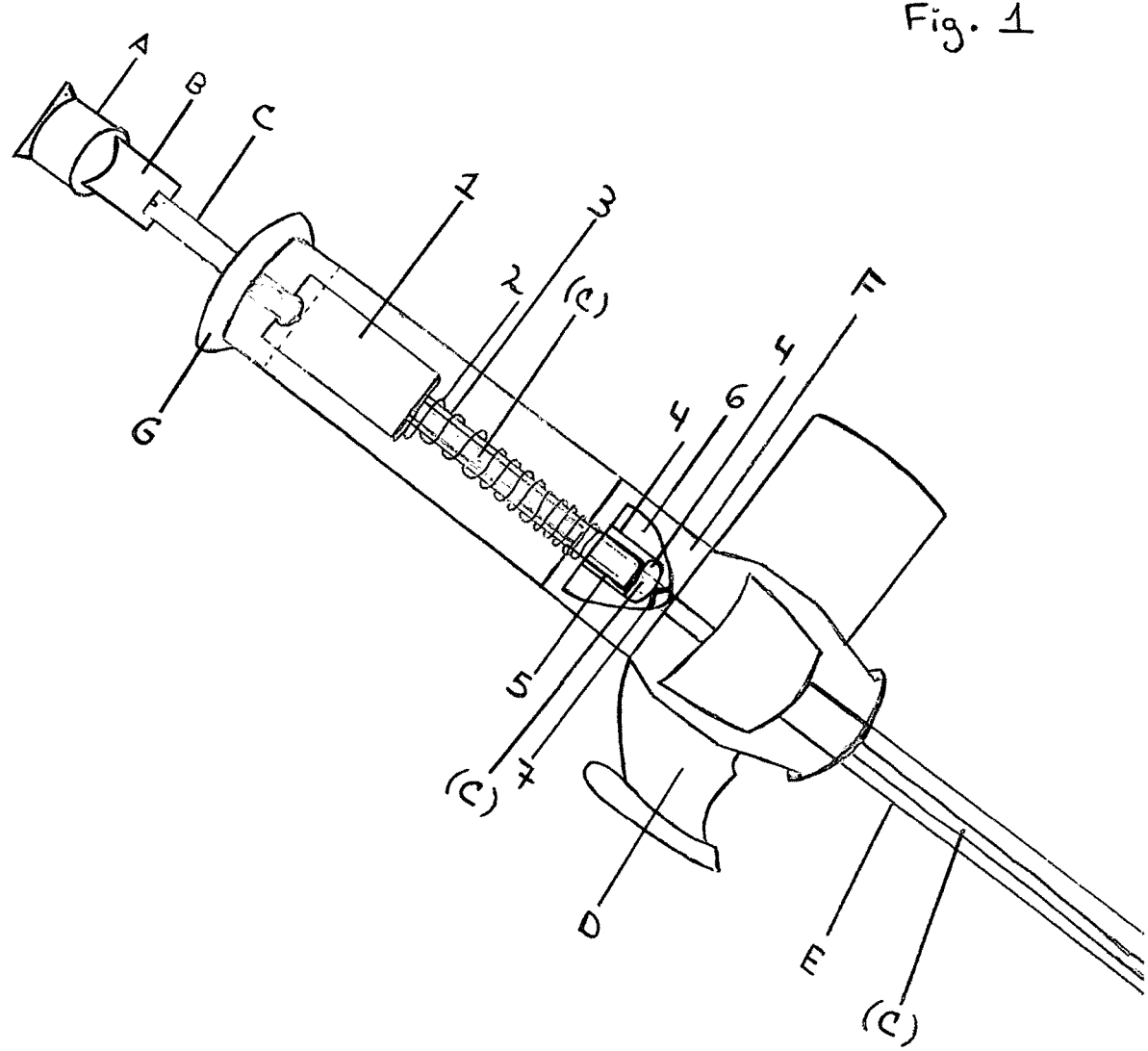
FIG. 1. Illustrates a Full View a the Peripheral Intravenous Catheter with an Internal Bi-valve System. The External structure with its basic conformation is alphabetically labeled from (A) to (G), while the internal structures conforming the Bi-Valve mechanism is numerated from 1 to 7.
Figure 2:
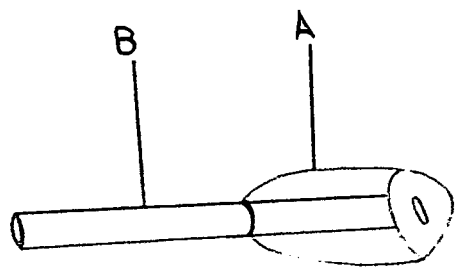
FIG. 2.
Figure 2:
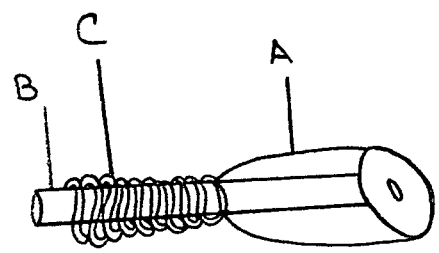
Figure 2:
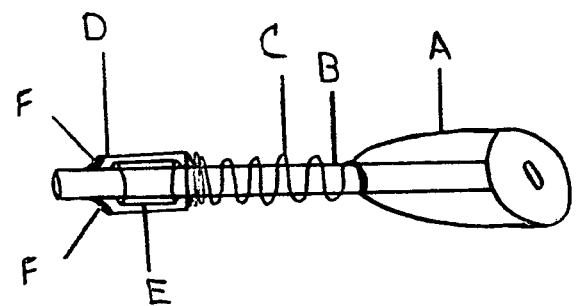
Figure 2:
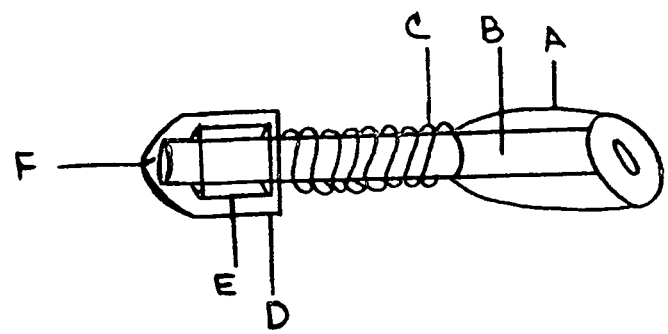
Figure 3:
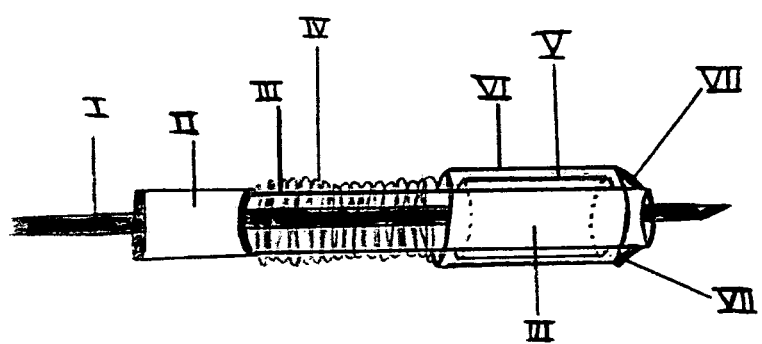
FIG. 3. Represents the joined structure of the Valve, the different parts of the internal valve are indicated in Roman Numerals from (I) to (VII). In this illustration the needle or guide wire (signaled with Roman Numeral: I) is added to the structure in order to represent and better understand its trajectory through the internal mechanism of the Valve.

DETAILED DESCRIPTION OF THE FIGURES
FIG. 1

Illustrates a full view of a peripheral intravenous catheter, the external structure with its basic conformation is alphabetically labeled from (A) to (G), while the internal structures conforming the bi-valve mechanism is numerated from 1 to 7.
(A) Represents the cap covering the security back flow chamber of the needle guide wire (a back flow chamber).
(B) Represents the needle or guide wire itself.
(C) Body of the needle or guide wire (seen in three different times along its trajectory passing through the internal mechanism all the way to the distal catheter) (a needle).
(D) Wings of the IV catheter used for manipulation illustrated in this case.
(E) Distal Catheter (a catheter shaft)
(F) Middle Chamber housing the silicon rubber valve.
(G) Connecting Cap of the catheter (a connecting cap)
Internal Mechanism Represented by Numbers 1 to 7
1. Proximal plastic or silicon sealing Adapter: has to be at a [small] minimal distance [distally] below the connecting end of the catheter, the proximal end connecting cap (G) allows the connection of intravenous infusion or 3 way stopcock This allows a two way or 3 way stopcock to adjust to the proximal end of the catheter and at the same time adapting and sealing to the proximal Plastic connector or silicon seal connection adapter. This activates the internal mechanism by pushing it distally with the help resistance support of the Teflon made or stainless steal mini-spiral spring band and displacing the plastic or stainless steal made tube guide distally and opening the valve located in the middle chamber (a sealing cap adapter).
2. Teflon made or stainless steal made mini-spiral spring band [metal spiral spring] (a spring)
3. Plastic or stainless steal tube [chamber] guide, harboring the needle or guide wire, and once the needed or guide wire is retracted the plastic or stainless steal tube guide works as a passage to administer infusions or medications (a tubular guide).
Middle Chamber (F)
4. Plastic Guide located and internalized inside the silicon rubber valve and working as an internal skeleton of the valve by allowing and facilitating the plastic or stainless steal tube guide to slide within the body of the valve allowing it to open and close the valve (a supporting tube).
5. Illustration of the Distal end of the plastic or stainless steal tube guide contained and housed inside the plastic guide skeleton of the body of the silicon rubber valve.
6. Silicon Rubber valve (a flexible valve).
7. Bi-valve opening

FIG. 2

Shapes of the drawings are NOT essential to the invention.
Here the entire Internal Mechanism is Reconstructed.
A. plastic or silicon sealing cap Adapter
B. Plastic [tube] or stainless steal tubular guide (which harbors the extracting needle or guide wire of any system catheter implied.
C. Mini-spiral [metal] spring band (made out of Teflon or stainless steal).
D. Silicon Rubber Body component of the valve
E. Plastic Guide located inside the silicon rubber Body of the valve and functioning as an internal skeleton which allows and facilitates the plastic or stainless steal Tube guide to slide inside the silicon rubber valve opening and closing the distal Bi-Valve access.
F. Distal Bi-Valve access

FIG. 3:

Illustrates a structural view of the adaptable internal Bi-valvular secure system. The external structure with its basic conformation is labeled in roman numerals from I-VII
I. Represents the retractable needle or any type of catheter guide.
II. Represents the proximal cap adaptable to any external line. This proximal portion of the devise seals the connection with any type of external port and opening an access for fluid or therapeutic administration of substance by activating the sliding mechanism of the devise in conjunction with the resistance control mechanism of the Teflon type/stainless steal mini-spiral that serves as a support base proximally (at the base) of the proximal cap, and stands distally at the roof base of the silicon rubber component, as the mini-spiral surrounds the plastic/Teflon or stainless steal tube guide it will allow it to slide inside the mini-spiral through the internal plastic skeleton of the the silicon rubber body component by allowing the tube guide to enter the silicon valve reaching the distal part of the silicon component and activating the valvular aspect of the silicon by pushing it open from inside out through the sliding mechanism supported by the mini spiral, and, in the same fashion, closing the valve the sliding retraction of the tube guide when disconnecting an external port or line in between uses.
III. Represents the Internalized sliding tube guide which can consist of Plastic, Teflon, or Stainless Metal and its function as explained in Num. II description.
VI. Represents the Mini-spiral support which can be made out of Teflon or Stainless Steal. Its function explained in Num. II description.
V. Represents the internalized plastic skeleton of the silicon component that serves as a way through allowing the tubular guide to slide into the internal aspect of the silicon component in order to reach the distal part of the silicon and activating the opening and closure of the valve through this unique sliding mechanism.
VI. Silicon body of the valve harboring the plastic skeleton through which the tubular guide slides through.

VII. Represents the Bi-Valvular access of the silicon component which is activated by opening and closing through the sliding mechanism during and in between uses of any type of system catheter.

The invention claimed is:

1. A catheter, comprising:
a catheter shaft connected to a connecting cap via a catheter body extending along an axis from said connecting cap to said catheter shaft; and
a bi-valve assembly disposed within said catheter body, said bi-valve assembly comprising: a tubular guide member, a spring, a sealing cap adapter, a supporting tube, and a flexible valve;
wherein said flexible valve is fixedly adjoined to a proximal mouth of said catheter shaft and internally supported by said supporting tube, said flexible valve having a flexible perforation penetrable by said tubular guide and configured to return back to a sealed position when said tubular guide is pulled away from said flexible valve,
wherein said tubular guide is movably installed within said body to allow movement on an axis from said connecting cap to said proximal mouth of said shaft mouth, and having said sealing cap adapter fixed around a proximal end of said tubular guide,
wherein said tubular guide is surrounded by said spring while said spring is held between said sealing cap adapter and said supporting tube, said spring is configured to push said tubular guide proximally towards said connecting cap and away from said flexible valve,
wherein the tubular guide and sealing cap adapter are made of different materials.

2. The catheter of claim 1, wherein said connecting cap is adaptable to an external line.

3. The catheter of claim 2, wherein adapting of said connecting cap to the external line pushes said sealing cap adapter, thereby pushing said tubular guide to slide through said supporting tube towards said proximal mouth of said catheter shaft to the extent of penetrating through said flexible perforation in said flexible valve, thereby forming a hollow passage between the external line adapted to said connecting cap and said proximal mouth of said catheter shaft.

4. The catheter of claim 3, wherein the disengagement of the external line from said connecting cap allows said spring to extend and push said tubular guide to slide back towards said connecting cap, which in turn allows said flexible perforation in said flexible valve to return back to the sealed position, thereby preventing passage of substances through said proximal mouth of said catheter shaft.

5. A catheter with a bi-valve assembly, comprising:
a. a catheter shaft;
b. a connecting cap;
c. a catheter body extending along an axis from said connecting cap to said catheter shaft with a hub located in said catheter body containing a bi-valve assembly, said bi-valve assembly comprising:
a stainless steel tubular guide;
a spring; and
a silicon sealing cap adapter;
a supporting tube; and
a flexible valve;
wherein said flexible valve is fixedly adjoined to a proximal mouth of said catheter shaft and internally supported by said supporting tube, said flexible valve having a flexible perforation penetrable by said tubular guide and configured to return back to a sealed position when said tubular guide is pulled away from said flexible valve, wherein the flexible perforation opens sideward,
wherein said tubular guide is movably installed within said hub to allow movement on an axis from said connecting cap to said proximal mouth of said catheter shaft mouth, and having said sealing cap adapter fixed around a proximal end of said tubular guide,
wherein said tubular guide is surrounded by said spring while said spring is held between said silicon sealing cap adapter and said supporting tube, said spring is configured to push said tubular guide proximally towards said connecting cap and away from said flexible valve,
wherein said connecting cap is adaptable to an external line,
wherein adapting of said connecting cap to the external line pushes said silicon sealing cap adapter, thereby pushing said tubular guide to slide through said supporting tube towards said proximal mouth of said catheter shaft to the extent of penetrating through said flexible perforation in said flexible valve, thereby forming a hollow passage between the external line adapted to said connecting cap and said proximal mouth of said catheter shaft, and
wherein the disengagement of the external line from said connecting cap allows said spring to extend and push said tubular guide to slide back towards said connecting cap, which in turn allows said flexible perforation in said flexible valve to return back to the sealed position, thereby preventing passage of substances through said proximal mouth of said catheter shaft.

6. The catheter of claim 5, further comprising a needle, wherein said needle is threaded through the catheter.

7. The catheter of claim 6, wherein said needle enters the catheter from said connecting cap and passes through said tubular guide and exits from a distal mouth of said catheter shaft.

8. The catheter or claim 7, wherein removal of said needle allows said flexible perforation in said flexible valve to automatically close and seal, thereby preventing passage of substances through said proximal mouth of said catheter shaft.

9. The catheter of claim 6, further comprising a transparent back flow chamber coupled to proximal end of said needle, said transparent back flow chamber is capable of visibly receiving a flow of substance entering through distal end of said needle, thereby indicating a penetration position of said needle.

10. The catheter of claim 5, wherein said flexible perforation is configured as a longitudinal slit in said flexible valve.

11. The catheter of claim 5, wherein the tubular guide and sealing cap adapter are made of different materials.

12. The catheter of claim 5, wherein the tubular guide is pushed through the valve while maintaining its shape, and wherein the sealing cap adapter is configured to flexibly adjust to the inner wall of the catheter body thereby creating sealing between the internal flow path of the tubular guide and its external mechanical area.

13. The catheter of claim 5, wherein a diameter of the silicon cap adapter is slightly wider than a diameter of the internal wall of the catheter hub.

14. The catheter of claim 13, wherein pushing the silicon cap adapter into the catheter hub will cause it to slightly compress to fit tightly into the internal wall of the catheter hub.

15. The catheter of claim 5, wherein the catheter is modular.

16. The catheter of claim 5, wherein the silicon is thick and flexible and expands tightly toward the internal walls of the catheter to provide reliable, efficient and long-lasting sealing regardless of deviations in the internal surface of the catheter.

17. A bi-valve assembly comprising:
- a stainless steel tubular guide;
- a spring; and
- a silicon sealing cap adapter;
- a supporting tube; and
- a flexible valve;
- wherein said sealing cap adapter is fixed on the proximal segment of said tubular guide, said flexible valve is suspended around the distal segment of said tubular guide and internally supported by said supporting tube such that said flexible valve is covering the distal opening of said tubular guide,
- wherein said flexible valve having a flexible perforation penetrable by said tubular guide and configured to return back to a sealed position when said tubular guide is pulled away from said flexible valve,
- wherein said tubular guide is surrounded by said spring while said spring is held between said sealing cap adapter and said supporting tube, said spring is configured to push said tubular guide proximally towards said connecting cap and away from said flexible valve.

18. The bi-valve assembly of claim 17, wherein the bi-valve assembly is installable inside a hub of a catheter, said catheter comprising a catheter shaft and a connecting cap adaptable to an external line, such that said tubular guide is movably installed within said hub to allow movement on an axis from said connecting cap to the proximal mouth of said catheter shaft, and
- wherein adapting of said connecting cap to the external line pushes said sealing cap adapter, thereby pushing said tubular guide to slide through said supporting tube and towards said proximal mouth of said catheter shaft to the extent of penetrating through said flexible perforation in said flexible valve, thereby forming a hollow passage between the external line adapted to said connecting cap and said proximal mouth of said catheter shaft, and
- wherein the disengagement of the external line from said connecting cap allows said spring to extend and push said tubular guide to slide back towards said connecting cap, which in turn allows said flexible perforation in said flexible valve to return back to the sealed position, thereby preventing passage of substances through said proximal mouth of said catheter shaft.

* * * * *